United States Patent [19]

Merz et al.

[11] 3,981,874

[45] Sept. 21, 1976

[54] N-[(METHOXYMETHYL-FURYL)-METHYL]-MORPHINANS OR -6,7-BENZOMORPHANS AND SALTS THEREOF

[75] Inventors: Herbert Merz; Adolf Langbein, both of Ingelheim am Rhein; Gerhard Walther; Klaus Stockhaus, both of Bingen (Rhine), all of Germany

[73] Assignee: Boehringer Ingelheim GmbH, Ingelheim am Rhein, Germany

[22] Filed: Oct. 15, 1974

[21] Appl. No.: 514,474

[30] Foreign Application Priority Data
Oct. 27, 1973 Germany............................ 2354002

[52] U.S. Cl............................ 260/293.54; 260/285; 260/DIG. 13; 424/260; 424/267
[51] Int. Cl.².................................... C07D 221/26
[58] Field of Search................ 260/293.54, DIG. 13

[56] References Cited

UNITED STATES PATENTS

| | | | |
|---|---|---|---|
| 3,632,591 | 1/1972 | Albertson et al. | 260/293.54 |
| 3,823,150 | 7/1974 | Merz et al. | 260/293.54 |
| 3,833,595 | 9/1974 | Atsumi et al. | 260/293.54 |

*Primary Examiner*—G. Thomas Todd
*Attorney, Agent, or Firm*—Hammond & Littell

[57] ABSTRACT

Compound of the formula

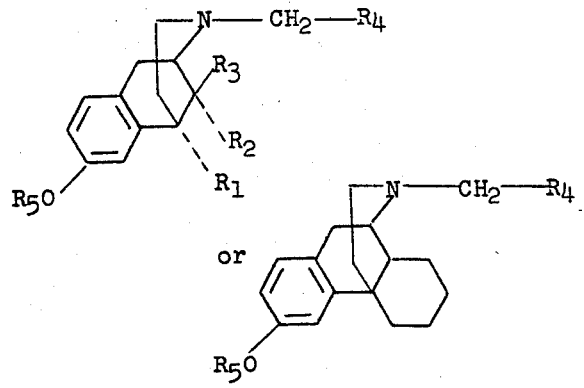

wherein
$R_1$ and $R_2$, which may be identical to or different from each other, are each hydrogen or alkyl of 1 to 3 carbon atoms,
$R_3$ is hydrogen or methyl,
$R_4$ is

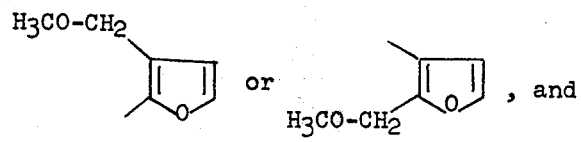 , and $R_5$ is hydrogen, methyl or acetyl, and non-toxic, pharmacologically acceptable acid addition salts thereof; the compounds as well as their salts are useful as analgesics.

6 Claims, No Drawings

N-[(METHOXYMETHYL-FURYL)-METHYL]-MORPHINANS OR -6,7-BENZOMORPHANS AND SALTS THEREOF

This invention relates to novel N-[(methoxymethyl-furyl)-methyl]-morphinans or -6,7-benzomorphans and acid addition salts thereof, as well as to various methods of preparing these compounds.

More particularly, the present invention relates to a novel class of benzomorphan and morphinan derivatives represented by the formulas

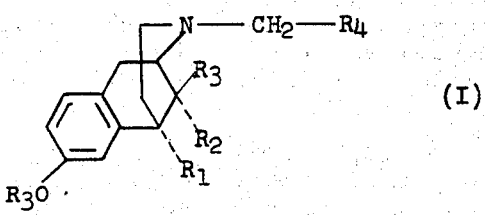

(I)

and

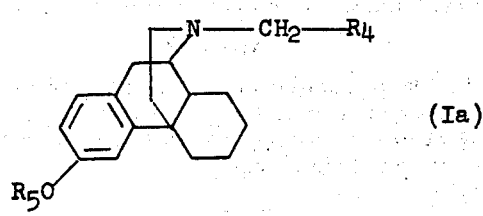

(Ia)

wherein
$R_1$ and $R_2$, which may be identical to or different from each other, are each hydrogen or alkyl of 1 to 3 carbon atoms,
$R_3$ is hydrogen or methyl,
$R_4$ is

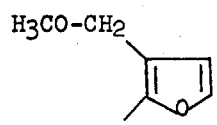 or 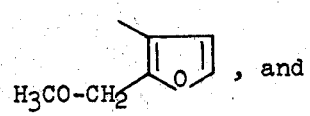, and $R_5$ is hydrogen, methyl or acetyl, and their non-toxic, pharmacologically acceptable acid addition salts.

A particularly preferred subgenus thereunder is constituted by those compounds of the formulas I and Ia wherein $R_1$, $R_2$, $R_3$ and $R_4$ have the meanings previously defined, and $R_5$ is hydrogen.

When $R_1$ and/or $R_2$ in formula I are alkyl, they are in the cis-configuration; in other words, those compounds are α-benzomorphans.

The compounds of the formulas I and Ia occur in stereoisomeric forms; consequently the present invention relates to the racemates as well as to the optically active antipodes, preferably the (—)-stereoisomers, of these compounds.

The compounds embraced by formulas I and Ia may be prepared by various methods involving known chemical synthesis principles, among which the following have proved to be particularly convenient and efficient.

Method A

By alkylating a norberzomorphan of the formula

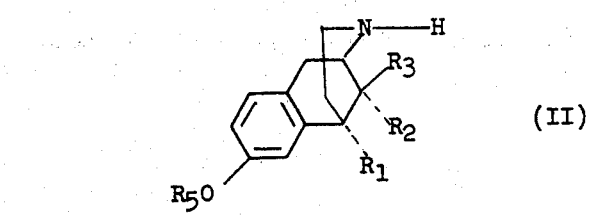

(II)

or a normorphinan of the formula

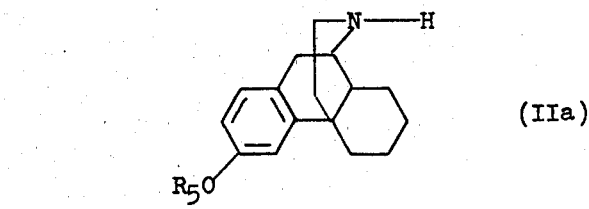

(IIa)

wherein R₁, R₂, R₃ and R₅ have the same meanings as in formulas I and Ia, with a compound of the formula

wherein

R₄ has the same meanings as in formulas I and Ia, and

Y is a nucleophilically removable group, preferably halogen, and especially chlorine, bromine or iodine, arylsulfonyloxy, aralkylsulfonyloxy, alkylsulfonyloxy or trialkylammonium.

The alkylation is performed with the calculated amount or an excess of thereover of the alkylating agent of the formula III, and advantageously in the presence of an acidbinding agent, such as triethylamine, N,N-dichlohexyl-ethylamine, sodium carbonate, calcium carbonate or, most preferably, sodium bicarbonate. It is also of advantage to perform the reaction in an inert solvent medium, such as chloroform, methylene chloride, benzene, acetone, dioxane, tetrahydrofuran, dimethylformamide or mixtures of any two or more of these, especially mixtures of tetrahydrofuran and dimethylformamide. The reaction temperature is variable within wide limits, but a temperature between 0°C and the boiling point of the particular solvent medium which is employed is preferred.

Method B

By reducing a carbonamide or thioamide of the formula

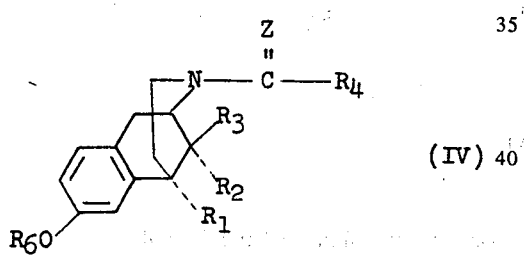

or

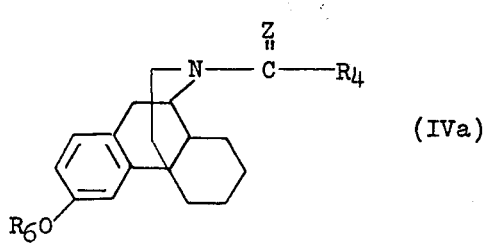

wherein

R₁, R₂, R₃ and R₄ have the same meanings as in formulas I and Ia,

R₆ is hydrogen, methyl or acyl, and

Z is oxygen or sulfur.

The reduction of a carbonamide of the formula IV or IVa (Z = oxygen) may be effected by various methods. Most advantageous is the reduction with a complex hydride of high reducing power, especially with lithium aluminum hydride. The complex hydride is provided in the calculated amount or in excess thereover, preferably up to double the calculated amount. The reduction is advantageously performed in an inert solvent medium, preferably diethyl ether, diisopropyl either or especially tetrahydrofuran. The reaction temperature is variable within wide limits, but a temperature between 0°C and the particular solvent medium which is used is preferred.

If the reduction with a complex hydride, such as lithium aluminum hydride, is applied to a carbonamide of the formula IV or IVa wherein R₆ is acyl, not only the carbonyl group is reduced, but also the acyl group is simultaneously split off, yielding the corresponding compound of the formula I or Ia wherein R₅ is hydrogen.

The reduction of a thioamide of the formula IV or IVa (Z = sulfur) proceeds considerably more readily than the reduction of a carbonamide. For instance, it can be effected with a complex hydride, or also with a nascent hydrogen generated, for example, by Zn/hydrochloric acid, Zn/acetic acid or aluminum amalgam/-water; it is further possible to effect the conversion by catalytic hydrogenation in the presence of Raney nickel, or electrochemically. As in the case of O-acyl derivatives of the carbonamides, the reduction of a thioamide of the formula Iv or IVa wherein R₆ is acyl with a reducing agent of high reducing power simultaneously splits off the acyl group, yielding a compound of the formula I or Ia wherein R₅ is hydrogen.

Method C

For the preparation of a compound of the formula I of Ia wherein R₅ is methyl or acetyl, by methylating an N-[(hydroxymethyl-furyl)-methyl]-benzomorphan or morphinan of the formula

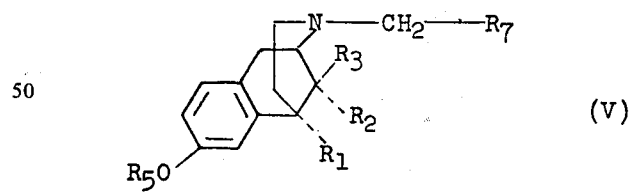

or

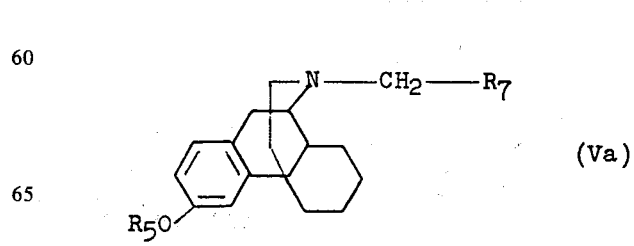

wherein $R_1$, $R_2$, $R_3$ and $R_5$ have the same meanings as in formulas I and Ia, and $R_7$ is

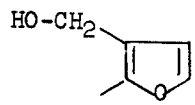 or 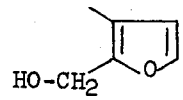, or an alcoholate thereof.

The methylation may be effected in various ways; for instance, dimethylsulfate, methyl iodide, diazomethane or a phenyltrimethylammonium halide may be used as the methylating agent. Instead of a free alcohol of the formula V or Va, it is advantageous to use a corresponding alkali metal alcoholate, such as the sodium alcoholate, as the starting material. The alcoholate does not need to be isolated and can be methylated in situ in the reaction solution wherein it is formed. Sodium hydride has proved to be particularly suitable for the preparaton of the alcoholate.

The methylation reaction is advantageously performed in an inert solvent medium, such as in tetrahydrofuran or dioxane, and, although the reaction temperature is not a critical factor, a temperature between 0° and 100°C is preferred.

In those instances where the starting compound of the formula V or Va is one wherein $R_5$ is hydrogen (a free phenolic hydroxyl group), not only the alcoholic hydroxyl group in the N-substituent is methylated, but also the phenolic hydroxyl group, yielding a compound of the formula I or Ia wherein $R_5$ is methyl.

Method D

For the preparation of a compound of the formula I or Ia wherein $R_5$ is acetyl, by acetylating the corresponding compound of the formula I or Ia wherein $R_5$ is hydrogen.

The acetylation is performed with an activated acetic acid derivative, such as with an acetyl halide, preferably with acetyl chloride, or with acetic acid anhydride. It is advantageously performed in an inert solvent medium or, particularly in the case of acetic acid anhydride, an excess of the acetylating reagent may be used as the solvent medium. Pyridine is an example of a suitable solvent medium or an additive to other solvents. The reaction temperature range is from 20° to 150°C, preferably from 50° to 90°C.

The majority of the starting compounds needed for methods A through D are known compounds. For example, the norbenzomorphans and normorphinans of the formulas II and IIa have been repeatedly described in the literature.

However, the alkylating agents of the formula III needed for method A are novel and may, for example, be prepared in the following manner:

Starting from 2-methyl-3-ethoxycarbonyl-furan of the formula VI below, which is described in *Organic Synthesis*, Collective Volume IV, page 649, 2-methoxymethyl-3-chloromethyl-furan is obtained by means of the following schematic reaction sequence:

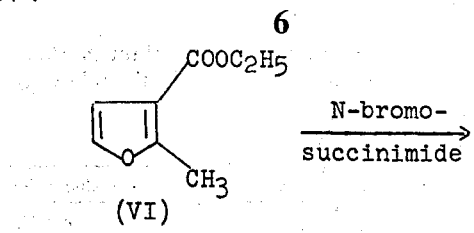

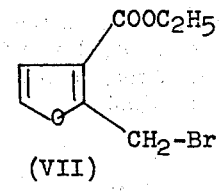

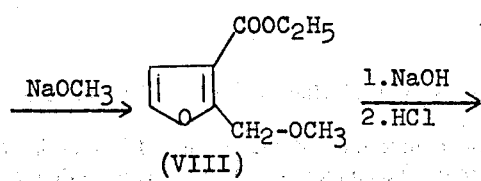

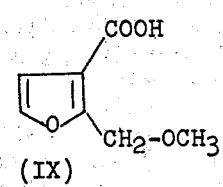

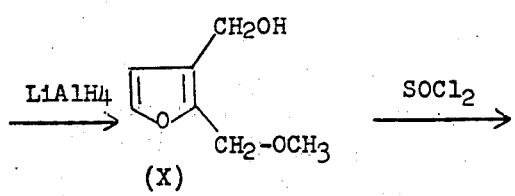

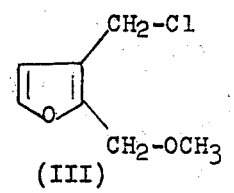

The yields and melting or boiling points of the intermediates and the end product are shown in the following table.

TABLE I

| Compound | Yield | Melting point | Boiling point |
|---|---|---|---|
| VII | 80% | | 94–96°C/0.3 mm Hg |
| VIII | 85% | | 106–109°C/14 mm Hg |
| IX | 90% | 80–83°C | |
| X | 75% | | 122–124°C/14 mm Hg |
| III | 59% | | 96–103°C/14 mm Hg |

In analogous fashion, 2-chloromethyl-3-methoxymethyl-furan (III; Y=Cl, $R_4$=3-methoxymethyl-furfuryl) may be prepared starting from 2-ethoxycarbonyl-3-methyl-furan of the formula

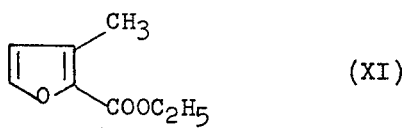

(XI)

the preparation of which is described in J.A.C.S. 82, 1433 (1950).

Those compounds of the formula III wherein Y is chlorine can be converted into the corresponding compounds wherein Y is bromine or iodine by the Finkelstein Substitution [H. Finkelstein, Berichte 43, 1528 (1910)]. Those compounds of the formula III wherein Y is halogen may, in turn, be converted into the corresponding sulfonates by reaction with a sulfonic acid salt; or by reaction of the halomethyl compounds with a tertiary amine the corresponding quaternary ammonium salts can be obtained.

A carbonamide of the formula IV or IVa may be obtained by reacting a nor-compound of the formula II or IIa with the corresponding methoxymethyl-substituted furan-carboxylic acid chloride. 3-Methoxymethyl-2-furan-carboxylic acid chloride, which is not described in the literature, may be prepared, starting from 2-ethoxy-carbonyl-3-methyl-furan of the formula XI above, by the following schematic reaction sequence:

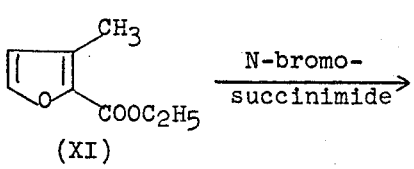

(XI)

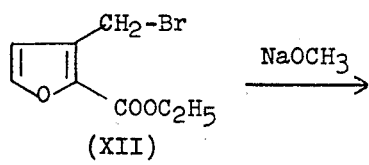

(XII)

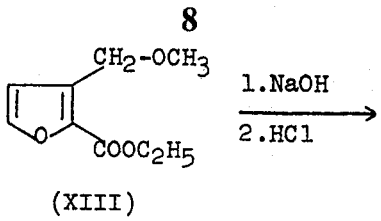

(XIII)

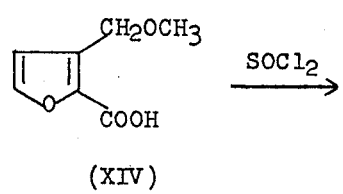

(XIV)

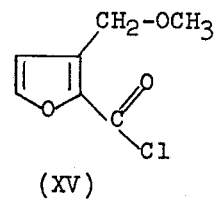

(XV)

The yields and melting or boiling points of the intermediates and end product of this reaction sequence are shown in the following table:

TABLE II

| Compound | Yield | Melting point | Boiling point |
|---|---|---|---|
| XII | 65% | | 70–77°C/0.3 mm Hg |
| XIII | 88% | | 117–120°C/16 mm Hg |
| XIV | 86% | 147–148°C | |
| XV | 89% | | 111–112°C/16 mm Hg |

The isomeric 2-methoxymethyl-3-furan-carboxylic acid chloride, b.p. 105°–106°C at 14 mm Hg, may be obtained in analogous manner with a yield of 77% by reacting 2-methoxymethyl-3-furancarboxylic acid of the formula IX above with thionyl chloride.

The thioamides of the formula IV or IVa (Z = sulfur) may be prepared by reacting a corresponding carbonamide of the formula IV or IVa (Z = oxygen) with phosphorus pentasulfide.

The starting compounds of the formula V or Va for method C may be prepared by reacting a corresponding norcompound of the formula II or IIa with an ethoxycarbonylhalomethyl-furan of the formula VII or XII to form the corresponding N-(ethoxycarbonyl-furylmethyl)-benzomorphan or -morphinan, and reducing the latter with lithium aluminum hydride.

The compounds embraced by formulas I and Ia are organic bases and therefore form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, pyruvic acid, tartaric acid, citric acid, malic acid, benzoic acid, p-hydroxybenzoic acid, salicylic acid, p-amino-benzoic acid, phthalic acid, cinnamic acid, ascorbic acid, 8-chlorotheophylline, methanesulfonic acid, ethanephosphonic acid or the like.

The following examples illustrate the present invention and will enable others skilled in the art to understand it more completely. It should be understood, however, that the invention is not limited solely to the particular examples given below.

EXAMPLE 1

5,9α-Dimethyl-2-[2-(methoxy-methyl)-furyl-(3)-methyl]-2'-hydroxy-6,7-benzomorphan and its methanesulfonate by method A A mixture consisting of 1.63 gm (7.5 millimols) of 5,9α-dimethyl-2'-hydroxy-6,7-benzomorphan, 1 gm of sodium bicarbonate, 1.31 gm (8.25 millimols) of 3-chloromethyl-2-methoxymethyl-furan, 10 ml of absolute dimethylformamide and 15 ml of absolute tetrahydrofuran was refluxed for 4 hours, accompanied by stirring. Thereafter, the reaction mixture was evaporated in vacuo in a rotary evaporator, the residue was shaken with a mixture consisting of 35 ml of chloroform and 35 ml of water, the chloroform phase was separated, and the aqueous phase was extracted twice with 15 ml of chloroform each. The chloroform phases were combined, washed with 30 ml of water, dried over sodium sulfate and evaporated in vacuo, leaving as the residue the raw free base reaction product, i.e. 5,9α-dimethyl-2-[2-(methoxy-methyl)-furyl-(3)-methyl]-2'-hydroxy-6,7-benzomorphan.

The raw free base was dissolved in about 10 ml of methanol, the solution was acidified with 0.72 gm (7.5 millimols) of methanesulfonic acid, and then ether was added until the solution just began to turn cloudy, and the mixture was allowed to stand overnight in a refrigerator. Thereafter, the mixture was suction-filtered, the filter cake was washed first with about 5 ml of a mixture of methanol and ether (1:2) and then with 10 ml of ether, and the resulting crystalline product was dried first in the air and finally at 80°C. 2.9 gm (88.5% of theory) of the methanesulfonate of the formula

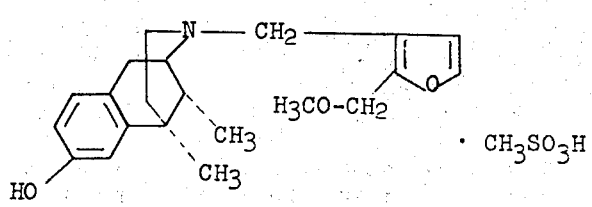

having a melting point of 220°–225°C were obtained. After recrystallization from methanol/ether it had a melting point of 224°–225°C.

EXAMPLE 2

5,9α-Dimethyl-2-[2-(methoxy-methyl)-furyl-(3)-methyl]-2'-methoxy-6,7-benzomorphan and its hydrochloride by method A A mixture consisting of 2.68 gm (0.01 mol) of 5,9α-dimethyl-2'-methoxy-6,7-benzomorphan hydrochloride, 1.75 gm (0.011 mol) of 3-chloromethyl-2-methoxymethyl-furan, 2.1 gm of sodium bicarbonate, 15 ml of dimethylformamide and 25 ml of tetrahydrofuran was refluxed for four hours, accompanied by stirring, and the reaction mixture was subsequently worked up as described in Example 1, yielding the raw free base, 5,9α-dimethyl-2-[2-(methoxy-methyl)-furyl-(3)-methyl]-2'-methoxy-6,7-benzomorphan.

The raw free base was dissolved in a small amount of absolute ethanol (about 10–15 ml), the solution was acidified with 4 ml of 2.5 N ethanolic hydrochloric acid, then ether was added until the solution just began to turn cloudy, and the mixture was allowed to stand overnight in a refrigerator to cause crystallization to go to completion. Thereafter, the mixture was suction filtered, the filter cake was washed first with a mixture of ethanol and ether (1:2) and then with ether, and the crystalline substance was dried initially in the air and subsequently at 80°C in a drying chamber. 2.5 gm (66% of theory) of the hydrochloride of the formula

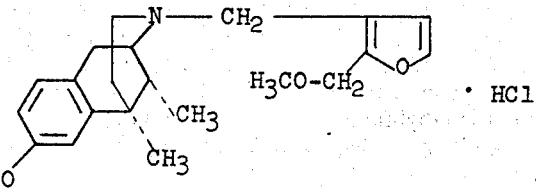

having a melting point of 140°–142°C were obtained. After recrystallization from ethanol/ether the melting point rose to 142°–144°C.

EXAMPLE 3

Using a procedure analogous to that described in Example 1, 5,9α-diethyl-2'-hydroxy-2-[2-(methoxymethyl)-furyl-(3)-methyl]-6,7-benzomorphan base and subsequently 2.8 gm (80% of theory) of the methanesulfonate, m.p. 172°–174°C, were obtained from 1.83 gm (7.5 millimols) of 5,9α-diethyl-2-hydroxy-6,7-benzomorphan and 1.32 gm of 2-methoxymethyl-3-chloromethyl-furan. After recrystallization from 90% methanol/ether, the methanesulfonate had a melting point of 173°–175°C.

EXAMPLE 4

Using a procedure analogous to that described in Example 1, 2'-hydroxy-2-[2-(methoxy-methyl)-furyl-(3)-methyl]-5-methyl-6,7-benzomorphan base and subsequently 1.8 gm (57% of theory) of the methanesulfonate, m.p. 160°–163°C, of the formula

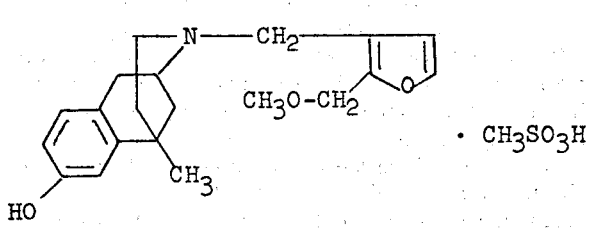

were obtained from 1.52 gm of 2'-hydroxy-5-methyl-6,7-benzomorphan and 1.32 gm of 2-methoxymethyl-3-chloromethyl-furan. The melting point of the methanesulfonate remained unchanged after recrystallization from ethanol/ether.

EXAMPLE 5

Using a procedure analogous to that described in Example 1, 2'-hydroxy-2-[2-(methoxy-methyl)-furyl-(3)-methyl]-5-n-propyl-6,7-benzomorphan base and subsequently 2.8 gm (82.5% of theory) of the merhanesulfonate, m.p. 187°–190°C, were obtained from 1.73 gm (7.5 millimols) of 2'-hydroxy-5-n-propyl-6,7-benzomorphan and 1.32 gm of 2-methoxymethyl-3-chloromethyl-furan. After recrystallization from ethanol/ether, the methanesulfonate had a melting point of 189°–191°C.

EXAMPLE 6

5,9α-Dimethyl-2-(3-methoxymethyl-furfuryl)-2'-hydroxy-6,7-benzomorphan by method B a. 5,9α-Dimethyl-2-(3-methoxymethyl-2-furoyl)-2'-hydroxy-6,7-benzomorphan 2.17 gm (0.01 mol) of 5,9α-dimethyl-2'-hydroxy-6,7-benzomorphan were dissolved in 70 ml of methanol by warming the solvent, and the solution was allowed to cool, whereupon, while vigorously stirring the solution, a mixture of 2.5 gm of potassium carbonate and 4 ml of water was added. The resulting suspension was admixed at 20°–25°C with a total of 1.92 gm (0.011 mol) of 3-methoxymethyl-2-furoyl chloride in five substantially equal portions over a period of 30 minutes, while vigorously stirring, and the resulting mixture was stirred for another hour. Thereafter, the methanol was removed by evaporation in vacuo, the residue was shaken with a mixture of 50 ml of chloroform and 50 ml of water, and the aqueous phase was separated and extracted twice with 25 ml of chloroform each. The chloroform solutions were combined, washed first with 20 ml of 2 N hydrochloric acid and then twice with 20 ml of water each, dried over sodium sulfate and evaporated in vacuo. The residue thus obtained consisted of raw 5,9α-dimethyl-2-(3-methoxymethyl-2-furoyl)-2'-hydroxy-6,7-benzomorphan which was used as such in the subsequent reduction.

b. The evaporation residue obtained in the preceding reaction step was dissolved in 40 ml of absolute tetrahydrofuran, and the solution was added dropwise over a period of one hour to a vigorously stirred suspension of 0.76 gm (0.02 mol) of lithium aluminum hydride in 20 ml absolute tetrahydrofuran in an ice bath. The resulting reaction mixture was allowed to warm to room temperature while stirring and was then refluxed for 2 hours. Thereafter, the reaction mixture was again placed on an ice bath and, while stirring it, first 1.5 ml of water and then 75 ml of a saturated aqueous solution of ammonium tartrate were added dropwise. The resulting mixture was vigorously shaken in a separating funnel, and the two phases were then allowed to separate therein. The tetrahydrofuran (upper) phase was isolated and evaporated in vacuo. The aqueous phase was extracted 3 times with 25 ml of chloroform each, the evaporation residue of the tetrahydrofuran phase was dissolved in the combined chloroform extracts, and the resulting solution was washed twice with 25 ml of water, dried over sodium sulfate and evaporated in vacuo. The residue was crystallized from 20 ml of ethanol and allowed to stand overnight in a refrigerator. Subsequently, the crystals were collected by suction filtration, washed with a little cold ethanol, and finally dried first in the air and then at 80°C, yielding 2.4 gm (70.5% of theory) of the compound of the formula

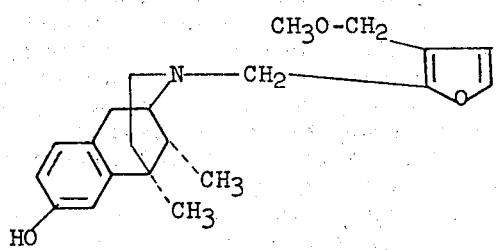

which had a melting point of 160°C. After recrystallization from 70% methanol it had a melting point of 161°C.

EXAMPLE 7

(−)-5,9α-Dimethyl-2-(3-methoxymethyl-furfuryl)-2'-hydroxy-6,7-benzomorphan and its hydrochloride by method B a. (−)-5,9α-Dimethyl-2-(3-methoxymethyl-2-furoyl)-2'-(3-methoxymethyl-2-furoyloxy)-6,7-benzomorphan A solution of 3.84 gm (0.022 mol) of 3-methoxymethyl-2-furoyl chloride was added dropwise over a period of one hour to a stirred suspension of 2.17 gm (0.01 mol) of (−)-5,9α-dimethyl-2'-hydroxy-6,7-benzomorphan in a mixture of 22 ml of methylene chloride and 4 ml of triethylamine, and the resulting mixture was refluxed for four hours. Thereafter, the reaction mixture was allowed to cool, and then, in the presence of ice, it was washed first twice with 20 ml of 2 N hydrochloric acid each and subsequently three times with 20 ml of water each. After drying over sodium sulfate, the methylene chloride solution was evaporated in vacuo, leaving as a residue raw (−)-5,9α-dimethyl-2-(3-methoxymethyl-2-furoyl)-2'-(3-methoxymethyl-2-furoyloxy)-6,7-benzomorphan which was used as such as the starting material for subsequent reaction sequence.

b. The raw product obtained in (a) was dissolved in 40 ml of tetrahydrofuran and then reduced with 1.2 gm of lithium aluminum hydride in a manner analogous to that described in Example 6 (b). The raw base obtained as the evaporation residue of the combined chloroform extracts was purified by chromatography on aluminum oxide. For this purpose the raw base was dissolved in 25 ml of chloroform, the solution was poured into a chromatography column charged with 40 gm of aluminum oxide (activity III, neutral), and the column was eluted with a mixture of 95 ml chloroform and 5 ml methanol. The eluate was collected in fractions of 20 ml each, the fractions were thin-layer chromatographically analyzed, and those fractions which contained the pure desired substance were combined and then evaporated in vacuo. The evaporation residue consisting of the purified base was converted into its hydrochloride and crystallized as described in Example 2, yielding 2.5 gm (66% of theory) of (−)-5,9α-dimethyl-2-(3-methoxymethyl-furfuryl)-2'-hydroxy-6,7-benzomorphan hydrochloride having a melting point of 158°C which remained unchanged after recrystallization from ethanol/ether. The specific rotation of the hydrochloride was $[\alpha]_D^{25} = -95°$ ($c = 1$, methanol).

EXAMPLE 8

Using a procedure analogous to that described in Example 7, 2.1 gm (55.5% of theory) of (+)-5,9α-dimethyl-2-(3-methoxymethyl-furfuryl)-2'-hydroxy-6,7-benzomorphan hydrochloride, m.p. 158°C (unchanged after recrystallization from ethanol/ether), specific rotation $[\alpha]_D^{25} = +95°$ ($c = 1$, methanol), were obtained by reacting 2.17 gm (0.01 mol) of (+)-5,9α-dimethyl-2'-hydroxy-6,7-benzomorphan with 3.84 gm of 3-methoxymethyl-furoyl chloride, reducing the reaction product with 1.2 gm of lithium aluminum hydride, and converting the base into its hydrochloride.

EXAMPLE 9

(−)-5,9α-Dimethyl-2'-hydroxy-2-[2-methoxymethyl-furyl-(3)-methyl]-6,7-benzomorphan was prepared in a manner analogous to that described in Example 6 by reacting 6.5 gm (0.03 mol) of (−)-5,9α-dimethyl-2'-hydroxy-6,7-benzomorphan with 5.75 gm of 2-methoxymethyl-3-furoyl chloride, and reducing the reaction product with 2.3 gm of lithium aluminum hydride. The base was then purified by column chromatography on silicagel, as described in Example 7, and then converted into its hydrochloride analogous to Example 2. 7.1 gm (63.2% of theory) of the hydrochloride, m.p. 218°–220°C (220°–221°C after recrystallization from ethanol/ether), specific rotation $[\alpha]_D^{25} = -72.2°$ ($c = 1$, methanol), were obtained.

EXAMPLE 10

(+)-5,9α-Dimethyl-2'-hydroxy-2-[2-methoxymethyl-furyl-(3)-methyl]-6,7-benzomorphan was prepared in a manner analogous to that described in Example 6 by reacting 2.17 gm (0.01 mol) of (+)-5,9α-dimethyl-2'-hydroxy-6,7-benzomorphan with 1.92 gm of 2-methoxymethyl-3-furoyl chloride, and reducing the reaction product with 0.76 gm of lithium aluminum hydride. The base was then converted into its hydrochloride, as described in Example 2, yielding 2.4 gm (63.8% of theory) of crystalline salt having a melting point of 220°–221°C (no change after recrystallization from ethanol/ether) and a specific rotation $[\alpha]_D^{25} = +72°$ ($c = 1$, methanol).

EXAMPLE 11

9α-Ethyl-2'-hydroxy-2-[3-methoxymethyl-furfuryl]-5-methyl-6,7-benzomorphan was prepared in a manner analogous to that described in Example 6 by reacting 2.31 gm (0.01 mol) of 9α-ethyl-2'-hydroxy-5-methyl-6,7-benzomorphan with 1.92 gm of 3-methoxymethyl-2-furoyl chloride, and reducing the reaction product with 0.76 gm of lithium aluminum hydride. The raw base was crystallized from a mixture of 50 ml methanol and 25 ml water (3.0 gm, m.p. 171°C), and then converted into its hydrochloride analogous to Example 2. 3.2 gm (81.5% of theory) of the hydrochloride, m.p. 224°C (unchanged after recrystallization from a mixture of 50 ml of ethanol, 5 ml water and 300 ml ether), were obtained.

EXAMPLE 12

5-Ethyl-2'-hydroxy-2-[3-methoxymethyl-furfuryl]-9α-methyl-6,7-benzomorphan was prepared in a manner analogous to that described in Example 6 by reacting 2.31 gm (0.01 mol) of 5-ethyl-2'-hydroxy-9α-methyl-6,7-benzomorphan with 1.92 gm of 3-methoxymethyl-2-furoyl chloride, and reducing the reaction product with 0.76 gm of lithium alumimum hydride. The raw base was crystallized from aqueous methanol. 3.2 gm (90% of theory) of the base, m.p. 128°–129°C (unchanged after recrystallization from a mixture of 30 ml methanol and 15 ml water), were obtained.

EXAMPLE 13

2'-Hydroxy-2-[3-methoxymethyl-furfuryl]-5-methyl-6,7-benzomorphan was prepared in a manner analogous to that described in Example 6 by reacting 2.03 gm (0.01 mol) of 2'-hydroxy-5-methyl-6,7-benzomorphan with 1.92 gm of 3-methoxymethyl-2-furoyl chloride, and reducing the reaction product with lithium aluminum hydride. The base was then converted into its hydrochloride analogous to Example 2. 2.0 gm (55% of theory) of the hydrochloride, m.p. 185°–186°C (186°–187°C after recrystallization from a mixture of 20 ml of ethanol and 30 ml ether), were obtained.

EXAMPLE 14

5-Ethyl-2'-hydroxy-2-[3-methoxymethyl-furfuryl]-6,7-benzomorphan was prepared in a manner analogous to that described in Example 6 by reacting 2.17 gm (0.01 mol) of 5-ethyl-2'-hydroxy-6,7-benzomorphan with 1.92 gm of 3-methoxymethyl-2-furoyl chloride, and reducing the reaction product with 0.76 gm of lithium aluminum hydride. The raw base was crystallized from a mixture of 50 ml methanol and 25 ml water (2.1 gm, m.p. 170°–171°C), and then converted into its hydrochloride analogous to Example 2. 2.3 gm (60.8% of theory) of the hydrochloride, m.p. 197°–198°C (unchanged after recrystallization from ethanol/ether), were obtained.

EXAMPLE 15

2'-Hydroxy-2-[3-methoxymethyl-furfuryl]-5-n-propyl-6,7-benzomorphan was prepared in a manner analogous to that described in Example 6 by reacting 2.31 gm (0.01 mol) of 2'-hydroxy-5-n-propyl-6,7-benzomorphan with 1.92 gm of 3-methoxymethyl-2-furoyl chloride, and reducing the reaction product with 0.76 gm of lithium aluminum hydride. The raw base was purified by column chromatography on aluminum oxide, as described in Example 7(b), and then converted into its oxalate. For this purpose, the purified base was dissolved in a little ethanol, the solution was acidified with an ethanolic oxalic acid solution, and then ether was added until the acidic solution just began to turn cloudy, whereupon the oxalate crystallized out. 1.75 gm (39.5% of theory) of the oxalate, m.p. 212°C (unchanged after recrystallization from a mixture of 30 ml ethanol and 2 ml water by addition of 40 ml ether), were obtained.

EXAMPLE 16

3.1 gm (84.3% of theory) of 3-hydroxy-N-(3-methoxymethyl-furfuryl)-morphinan, m.p. 163°C (unchanged after recrystallization from a mixture of 40 ml methanol and 15 ml water), of the formula

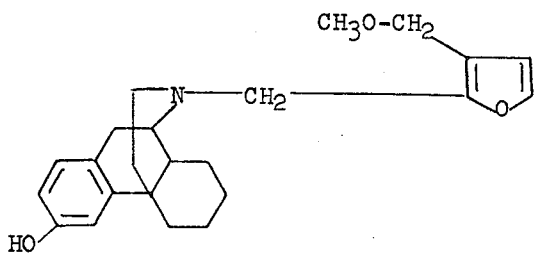

were obtained in a manner analogous to that described in Example 6 by reacting 2.43 gm (0.01 mol) of 3-hydroxy-morphinan with 1.92 gm of 3-methoxymethyl-2-furoyl chloride, reducing the reaction product with lithium aluminum hydride, and crystallizing the raw base from methanol/water.

EXAMPLE 17

3.2 gm (87.0% of theory) of (−)-3-hydroxy-N-(3-methoxymethyl-furfuryl)-morphinan, m.p. 135°–136°C (138°–139°C after recrystallization from a mixture of 20 ml methanol and 10 ml water), were obtained in a manner analogous to that described in Example 6 by reacting 2.43 gm (0.01 mol) of (−)-3-hydroxy-morphinan with 1.92 gm of 3-methoxymethyl-2-furoyl chloride, reducing the reaction product with lithium aluminum hydride, and crystallizing the raw base from methanol/water.

EXAMPLE 18

3.6 gm (97.7% of theory) of (+)-3-hydroxy-N-(3-methoxymethyl-furfuryl)-morphinan, m.p. 137°–138°C (138°–139°C after recrystallization from a mixture of 25 ml methanol and 10 ml water), were obtained in a manner analogous to that described in Example 6 by reacting 2.43 gm (0.01 mol) of (+)-3-hydroxy-morphinan with 1.92 gm of 3-methoxymethyl-2-furoyl chloride, reducing the reaction product with lithium aluminum hydride, and crystallizing the raw base from methanol/water.

EXAMPLE 19

9α-Ethyl-2'-hydroxy-2-[2-methoxymethyl-furyl-(3)-methyl]-5-methyl-6,7-benzomorphan was prepared in a manner analogous to that described in Example 6 by reacting 2.31 gm (0.01 mol) of 9α-ethyl-2'-hydroxy-5-methyl-6,7-benzomorphan with 1.92 gm of 2-methoxymethyl-3-furoyl chloride, and reducing the reaction product with 0.76 gm of lithium aluminum hydride. The raw base was purified by column chromatography on silicagel. For this purpose, the raw base was dissolved in 75 ml of chloroform, and the solution was introduced into a column prepared with 450 gm of silicagel and the flow agent chloroform/methanol/concentrated ammonia (90:10:0.5 ml). The column was then eluted with the indicated flow agent, and the eluate was collected in 50 ml-fractions. Those fractions containing the pure desired substance, as determined by thin-layer chromatography, were combined and evaporated in vacuo. The residue consisted of the purified base, which was crystallized from ether/petroleum ether (1.4 gm, m.p. 151°–152°C) and then converted into its hydrochloride analogous to Example 2. 1.5 gm (39.3% of theory) of the hydrochloride, m.p. 236°–238°C (unchanged after recrystallization from ethanol/ether), were obtained.

EXAMPLE 20

5-Ethyl-2'-hydroxy-2-[2-methoxymethyl-furyl-(3)-methyl]-9α-methyl-6,7-benzomorphan was prepared in a manner analogous to that described in Example 6 by reacting 2.31 gm (0.01 mol) of 5-ethyl-2'-hydroxy-9α-methyl-6,7-benzomorphan with 1.92 gm of 2-methoxymethyl-3-furoyl chloride, and reducing the reaction product with 0.76 gm of lithium aluminum hydride. The raw base was purified by column chromatography on silicagel, as described in Example 19, and then converted into its hydrochloride analogous to Example 2. 1.9 gm (48.5% of theory) of the hydrochloride, m.p. 104°–106°C (unchanged after recrystallization from ethanol/ether), were obtained.

EXAMPLE 21

2.4 gm (65.2% of theory) of 3-hydroxy-N-[2-methoxy-furyl-(3)-methyl]-morphinan, m.p. 128°–130°C (unchanged after recrystallization from benzene/petroleum ether), were obtained in a manner analogous to that described in Example 6 by reacting 2.43 gm (0.01 mol) of 3-hydroxy-morphinan with 1.92 gm of 2-methoxymethyl-3-furoyl chloride, reducing the reaction product with 0.76 gm of lithium aluminum hydride, and crystallizing the raw base from benzene/petroleum ether.

EXAMPLE 22

1.6 gm (43.5% of theory) of (−)-3-hydroxy-N-[2-methoxymethyl-furyl-(3)-methyl]-morphinan, m.p. 115°–116°C (116°–118°C after recrystallization from ether/petroleum ether), were obtained in a manner analogous to that described in Example 6 by reacting 2.43 gm (0.01 mol) of (−)-3-hydroxymorphinan with 1.92 gm of 2-methoxymethyl-3-furoyl chloride, reducing the reaction product with 0.76 gm of lithium aluminum hydride, and crystallizing the raw base from ether/petroleum ether.

EXAMPLE 23

2'-Hydroxy-2-[2-methoxymethyl-furyl-(3)-methyl]-5,9,9-trimethyl-6,7-benzomorphan was prepared in a manner analogous to that described in Example 6 by reacting 1.16 gm (5 millimols) of 2'-hydroxy-5,9,9-trimethyl-6,7-benzomorphan with 0.96 gm of 2-methoxymethyl-3-furoyl chloride, and reducing the reaction product with 0.38 gm of lithium aluminum hydride. The base was then converted into its methanesulfonate analogous to Example 1. 1.5 gm (66.5% of theory) of the methanesulfonate, m.p. 202°–204°C (unchanged after recrystallization from ethanol/ether), of the formula

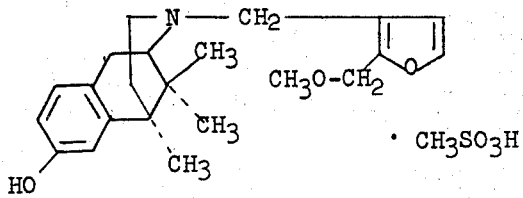

were obtained.

EXAMPLE 24

5,9α-Dimethyl-2'-methoxy-2-(3-methoxymethyl-furfuryl)-6,7-benzomorphan and its hydrochloride by method C a. 2-(3-ethoxy-carbonyl-furfuryl)-5,9α-dimethyl-2'-methoxy-6,7-benzomorphan A mixture consisting of 2.66 gm (0.01 mol) of 5,9α-dimethyl-2'-methoxy-6,7-benzomorphan, 2.1 gm of sodium bicarbonate and 2.6 gm (0.011 mol) of ethyl 2-bromomethyl-furan-3-carboxylate in a mixture of tetrahydrofuran and dimethylformamide was refluxed for 4 hours, accompanied by stirring. Thereafter, the reaction mixture was evaporated in vacuo, the residue was shaken with a mixture of 50 ml chloroform and 50 ml water, the aqueous phase was isolated in a separating funnel and again extracted with 25 ml of chloroform, and the combined chloroform extract solutions were washed with 40 ml of water, dried over sodium sulfate and evaporated in vacuo. The residue consisted of 2-(3-ethoxycarbonyl-furfuryl)-5,9α-dimethyl-2'-methoxy-6,7-benzomorphan.

b. 5,9α-Dimethyl-2-(3-hydroxymethyl-furfuryl)-2'-methoxy-6,7-benzomorphan hydrochloride The evaporation residue obtained in (a) was reduced with 1.2 gm of lithium aluminum hydride in a manner analogous to that described in Example 6(b), and the base reduction product was isolated as described in that example and then converted into its crystalline hydrochloride analogous to Example 2. 3.3 gm (87.5% of theory) of the hydrochloride, m.p. 191°C (unchanged after recrystallization from ethanol/ether), were obtained.

c. 1.0 gm (2.6 millimols) of the crystalline hydrochloride obtained in (b) was converted into the corresponding free base by shaking it with a mixture of 25 ml chloroform, 25 ml water and 5 ml 2 N ammonia, isolating the chloroform phase in a separating funnel, extracting the aqueous phase again with 25 ml of chloroform, combining the chloroform phases, and washing the organic solution with 25 ml of water, drying it over sodium sulfate and evaporating it in vacuo. The liberated base was dissolved in 15 ml of tetrahydrofuran, the solution was admixed with 0.24 gm of a 50% sodium hydride suspension in oil, the mixture was stirred for 10 minutes, 2.84 gm of methyl iodide were then added, and the resulting mixture was stirred for 2 hours more at room temperature. Thereafter, the reaction mixture was evaporated, the residue was shaken with a mixture of 25 ml chloroform and 25 ml water, the organic phase was isolated in a separating funnel, and the aqueous phase was again extracted with 25 ml of chloroform. The combined chloroform phases were washed with water, dried over sodium sulfate and evaporated in vacuo. The residue was purified in analogy to Example 19 by chromatography on silicagel (140 gm) using as the flow agent chloroform/methanol/ammonia (95:5:0.1). The purified base, 5,9α-dimethyl-2'-methoxy-2-(3-methoxymethyl-furfuryl)-6,7-benzomorphan, was then converted into its crystalline hydrochloride, yielding 0.5 gm (48.5% of theory) of the salt of the formula

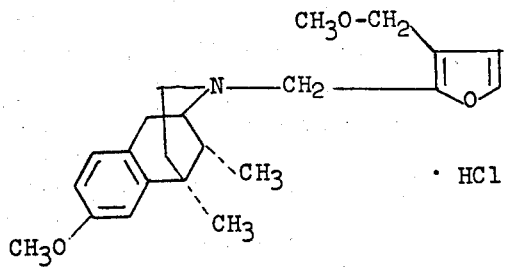

which had a melting point of 163°C (unchanged after recrystallization from ethanol/ether).

EXAMPLE 25

(+)-2'-Acetoxy-5,9α-dimethyl-2-(3-methoxymethyl-furfuryl)-6,7-benzomorphan and its oxalate by method D 0.7 gm of (+)-5,9α-dimethyl-2'-hydroxy-2-(3-methoxymethyl-furfuryl)-6,7-benzomorphan hydrochloride (see Example 8) was shaken with a mixture consisting of 25 ml of water, 5 ml of 2 N ammonia and 25 ml of chloroform, the chloroform phase was isolated in a separating funnel, and the aqueous phase was once again extracted with 25 ml of chloroform. The combined chloroform solutions were washed with water, dried over sodium sulfate and evaporated in vacuo. The residue consisted of the free base corresponding to the hydrochloride starting compound.

The free base thus obtained was admixed with 5 ml of acetic acid anhydride, and the mixture was heated for 30 minutes on a boiling water bath. Thereafter, the reaction mixture was evaporated in vacuo, and the residue was stirred for three minutes with a mixture of 20 ml water and 20 gm ice. Subsequently, 50 ml of ether were added, and the mixture was made alkaline by shaking it with 2 N ammonia in the presence of ice. The ether phase was now separated, the aqueous phase was again extracted with ether, and the combined ether extract solutions were washed with water, dried over sodium sulfate and evaporated in vacuo. The residue, (+)-2'-acetoxy- 5,9α-dimethyl-2-(3-methoxymethyl-furfuryl)-6,7-benzomorphan, was dissolved in a little absolute ethanol, the solution was acidified with oxalic acid, and then ether was added until the solution just began to turn cloudy. The crystalline substance which separated out was collected by suction filtration, the filter cake was washed first with ethanol/ether (1:1) and the with only ether, and the product was dried at 80°C. 0.4 gm of the oxalate, m.p. 86°–88°C (unchanged after recrystallization from ethanol/ether), were obtained.

The compounds of the present invention, that is, those embraced by formulas I and Ia above and their nontoxic, pharmacologically acceptable acid addition salts, have useful pharmacodynamic properties. More particularly, the compounds of this invention exhibit strong analgesic activities in warm-blooded animals, such as mice. In various pharmacological tests on mice, such as the Haffner test, the hot plate test and the writhing test, the analgesic activity of the compounds of the present invention was found to be the same as or in some instances even greater than that of morphine. However, they differ from morphine by the absence of the typical morphine side effects in mice, such as Straub's tail, running in circles and the like, which, according to current literature teachings, is strongly indicative of the absence of addictive properties [see, for example, I. Schemano et al, *A Rapid Screening Test for Potential Addiction Liability of New Analgesic Agents*, Toxicol. Appl. Pharmacol. 6, 334–339 (1964)].

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 5.0 mgm/kg body weight, preferably 0.41 to 1.25 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 26

Tablets

The tablet composition is compounded from the following ingredients:

| | | |
|---|---|---|
| 5,9α-Dimethyl-2-[2-methoxymethyl-furyl-(3)-methyl]-2'-hydroxy-6,7-benzomorphan methanesulfonate | 50.0 | parts |
| Lactose | 95.0 | " |
| Corn starch | 45.0 | " |
| Colloidal silicic acid | 2.0 | " |
| Soluble starch | 5.0 | " |
| Magnesium stearate | 3.0 | " |
| Total | 200.0 | parts |

Preparation:

The benzomorphan compound is intimately admixed with the lactose and the corn starch, the mixture is moistened with an aqueous 10% solution of the soluble starch, the moist mass is forced through a 1 mm-mesh screen, the resulting granulate is dried at 40°C, the dry granulate is admixed with the colloidal silicic acid, and the composition is compressed into 200 mgm-tablets in a conventional tablet making machine. Each tablet contains 50 mgm of the benzomorphan and is an oral dosage unit composition with very effective analgesic action.

EXAMPLE 27

Coated pills

The pill core composition is compounded from the following ingredients:

| | | |
|---|---|---|
| 5,9α-Dimethyl-(3-methoxymethyl-furfuryl)-2'-hydroxy-6,7-benzomorphan | 75.0 | parts |
| Lactose | 100.0 | " |
| Corn starch | 65.0 | " |
| Colloidal silicic acid | 2.0 | " |
| Soluble starch | 5.0 | " |
| Magnesium stearate | 3.0 | " |
| Total | 250.0 | parts |

Preparation:

The ingredients are compounded in the same manner as in Example 26, and the composition is compressed into 250 mgm-pill cores which are subsequently coated with a thin shell consisting essentially of a mixture of sugar, talcum and gum arabic and finally polished with beeswax. Each coated pill contains 75 mgm of the benzomorphan compound and is an oral dosage unit composition with very effective analgesic action.

EXAMPLE 28

Suppositories

The suppository composition is compounded from the following ingredients:

| | | |
|---|---|---|
| (-)-5,9α-Dimethyl-2-(3-methoxymethyl-furfuryl)-2'-hydroxy-6,7-benzomorphan hydrochloride | 50.0 | parts |
| Lactose | 200.0 | " |
| Suppository base (e.g. cocoa butter) | 1450.0 | " |
| Total | 1700.0 | parts |

Preparation:

The benzomorphan compound is intimately admixed with the lactose, and the mixture is blended with the aid of an immersion homogenizer into the suppository base which had previously been melted and cooled to about 40°C. 1700 mgm-portions of the composition are poured into cooled suppository molds and allowed to harden therein. Each suppository contains 50 mgm of the benzomorphan compound and is a rectal dosage unit composition with very effective analgesic action.

EXAMPLE 29

Hypodermic solution

The solution is compounded from the following ingredients:

| | | |
|---|---|---|
| (-)-5,9α-Dimethyl-2'-hydroxy-2-[2-methoxymethyl-furyl-(3)-methyl]-6,7-benzomorphan hydrochloride | 25.0 | parts |
| Sodium chloride | 5.0 | " |
| Double-distilled water   q.s.ad | 5000.0 | " |
| | | by vol. |

Preparation:

The benzomorphan compound and the sodium chloride are dissolved in the double-distilled water, the solution is filtered until free from suspended particles, and the filtrate is filled under aseptic conditions into 5 cc-ampules which are subsequently sterilized and sealed. Each ampule contains 50 mgm of the benzomorphan compound, and its contents are an injectable dosage unit composition with very effective analgesic action.

EXAMPLE 30

Drop solution

The solution is compounded from the following ingredients:

| | | |
|---|---|---|
| 3-Hydroxy-N-(3-methoxymethyl-furfuryl)-morphinan | 0.70 | parts |
| Methyl p-hydroxy-benzoate | 0.07 | " |
| Propyl p-hydroxy-benzoate | 0.03 | " |
| De-mineralized water q.s.ad | 100.00 | " |
| | | by vol. |

Preparation:

The morphinan compound and the p-hydroxy-benzoates are dissolved in the de-mineralized water, the solution is filtered, and the filtrate is filled into 100 cc-bottles. 10 ml of the solution contain 70 mgm of the morphinan compound and are an oral dosage unit composition with very effective analgesic action.

Analogous results are obtained when any one of the other compounds embraced by formulas I and Ia or a non-toxic, pharmacologically acceptable acid addition salt thereof, is substituted for the particular active ingredient in Examples 26 through 30. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

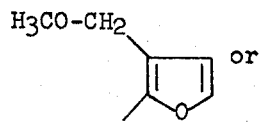

wherein
$R_1$ is methyl, ethyl or propyl,
$R_2$ is hydrogen, methyl or ethyl,
$R_3$ is hydrogen or methyl,
$R_4$ is $H_3CO-CH_2$ ⟨furyl⟩ or ⟨furyl⟩ $H_3CO-CH_2$ , and $R_5$ is hydrogen, methyl or acetyl, or a non-toxic, pharmacologically acceptable acid addition salt thereof.

2. A compound of claim 1, where $R_5$ is hydrogen, or a non-toxic, pharmacologically acceptable acid addition salt thereof.

3. A compound of claim 1, which is 5,9α-dimethyl-2-(3-methoxymethyl-furfuryl)-2'-hydroxy-6,7-benzomorphan or a non-toxic, pharmacologically acceptable acid addition salt thereof.

4. A compound of claim 1, which is (−)-5,9α-dimethyl-2-(3-methoxymethyl-furfuryl)-2'-hydroxy-6,7-benzomorphan or a non-toxic, pharmacologically acceptable acid addition salt thereof.

5. A compound of claim 1, which is 5,9α-dimethyl-2-[2-methoxymethyl-furyl-(3)-methyl]-2'-hydroxy-6,7-benzomorphan or a non-toxic, pharmacologically acceptable acid addition salt thereof.

6. A compound of claim 1, which is (−)-5,9α-dimethyl-2-[2-methoxymethyl-furyl-(3)-methyl]-2'-hydroxy-6,7-benzomorphan or a non-toxic, pharmacologically acceptable acid addition salt thereof.

* * * * *